(12) United States Patent
Rush

(10) Patent No.: US 7,449,313 B2
(45) Date of Patent: Nov. 11, 2008

(54) SYSTEMS AND PROCESSES FOR CELLULOSIC ETHANOL PRODUCTION

(76) Inventor: Stephen L. Rush, P.O. Box 543, San Bernardino, CA (US) 92410

( * ) Notice: Subject to any disclaimer, the term of this patent is extended or adjusted under 35 U.S.C. 154(b) by 0 days.

(21) Appl. No.: 12/014,090

(22) Filed: Jan. 14, 2008

(65) Prior Publication Data

US 2008/0102503 A1    May 1, 2008

Related U.S. Application Data

(63) Continuation-in-part of application No. 11/934,768, filed on Nov. 3, 2007, now abandoned.

(51) Int. Cl.
*C12P 7/10* (2006.01)
(52) U.S. Cl. .................................... 435/165
(58) Field of Classification Search .................. 435/165
See application file for complete search history.

(56) References Cited

U.S. PATENT DOCUMENTS

| | | | |
|---|---|---|---|
| 4,275,167 | A | 6/1981 | Wicklow et al. |
| 4,321,327 | A | 3/1982 | Chen et al. |
| 4,427,775 | A | 1/1984 | Chen et al. |
| 4,840,903 | A | 6/1989 | Wu |
| 5,677,154 | A | 10/1997 | Van Draanen et al. |
| 6,846,657 | B2 | 1/2005 | Heikkila et al. |
| 7,109,005 | B2 | 9/2006 | Eroma et al. |
| 2006/0177917 | A1 | 8/2006 | Warzywoda et al. |
| 2006/0246563 | A1 | 11/2006 | Eroma et al. |
| 2006/0275882 | A1 | 12/2006 | Martinez-Gutierrez et al. |
| 2007/0231869 | A1 | 10/2007 | Holmgren et al. |

FOREIGN PATENT DOCUMENTS

| | | |
|---|---|---|
| CN | 1880415 | 12/2006 |
| CN | 1880416 | 12/2006 |
| RU | 2037001 C1 | 6/1995 |
| WO | WO2007/072208 A2 * | 6/2007 |

OTHER PUBLICATIONS

Dijkerman et al. 1996. Cultivation of anaerobic fungi in a 10-l fermenter system for the production of (hemi-) cellulolytic enzymes. Applied Microbiology and Biotechnology, vol. 46, pp. 46:85-91.*

Bauchop et al.1981. Cellulose Fermentation by a Rumen Anaerobic Fungus in Both the Absence and the Presence of Rumen Methanogens. Applied and Environmental Microbiology, vol. 42, No. 6, pp. 1103-1110.*

Catino, Tom. 2006. Smart Economy: Algae bioreactor scrubs CO2 from power plant smokestacks to produce biofuels. http://smarteconomy.typepad.com/smart_economy/2006/10/algae_bioreacto.html, accessed on internet on Mar. 20, 2008.*

Sreenath et al. 2000. Production of ethanol from wood hydrolyzate by yeasts, Bioresource Technology, vol. 72, pp. 253-260.*

McKenna, Phillip, "From smokestack to gas tank", New Scientist (Oct. 7-Oct. 13, 2006) vol. 192, Iss. 2572; p. 28-29.*

Balan, V, Da Costa Sousa L., Chundawat SP, Vismeh R, Jones AD, Dale BE, "Mushroom Spent Straw: A Potential Substrate for an Ethanol-Based Biorefinery", Journal of Ind. Microbiol. Biotechnology, Jan. 8, 2008.

Chemical Abstract, 106:194798.
Chemical Abstract, 94:190290.
Chemical Abstract, 106:212501.
Chemical Abstract, 117:152995.
Chemical Abstract, 125:140617.
Chemical Abstract, 140:403103.
Chemical Abstract, 144:190716.

* cited by examiner

*Primary Examiner*—Jon P Weber
*Assistant Examiner*—Kailash C Srivastava
(74) *Attorney, Agent, or Firm*—Booth Udall, PLC

(57) ABSTRACT

A cellulosic ethanol production process. Implementations may include providing a raw cellulose stream by mixing a waste cellulose feed and an algae cellulose feed and hydrolyzing the raw cellulose stream to form a hydrolyzed cellulose stream by reacting the raw cellulose stream with one or more fungi from the phylum Neocallimastigomycota. Implementations may include liquefying the hydrolyzed cellulose stream to form a raw sugars stream, separating xylitol from the raw sugars stream and fermenting the sugars stream to form a raw ethanol stream by reacting the sugars stream with a yeast feed in at least one fermenter. Implementations also may include separating ethanol from the raw ethanol, generating an algae stream by reacting the xylitol stream with algae in at least one algae bioreactor, and reacting the algae stream in at least one biodiesel reactor to produce the algae cellulose feed and a biodiesel stream.

8 Claims, 2 Drawing Sheets

SYSTEMS AND PROCESSES FOR CELLULOSIC ETHANOL PRODUCTION

CROSS REFERENCE TO RELATED APPLICATIONS

This application is a continuation-in-part application of the earlier U.S. Utility patent application to Stephen LeRoy Rush entitled "Process For The Organic Breakdown of Cellulosic Tissue," application Ser. No. 11/934,768, filed Nov. 3, 2007, now abandoned, the disclosure of which is hereby incorporated entirely herein by reference.

BACKGROUND

1. Technical Field

Aspects of this document relate generally to processes for fuel production from biomass sources.

2. Background Art

The derivation of fuels from biomass sources has been in long practice. For example, ethanol and biodiesel derived from biomass sources are becoming increasingly adopted as fuel sources in internal combustion engines. Conventional ethanol generation technology involves processing a starchy source material (such as a grain or vegetable) by converting the starch source to free glucose and fermenting the glucose with yeast that excretes significant amounts of ethanol. Conventional biodiesel generation technology involves processing a feedstock, such as vegetable oil, through a reaction process such as transesterification to produce biodiesel and a variety of other byproducts. Other processes have been developed to generate a variety of other fuel-related materials from biomass, including lubricants, fuel additives, and greases.

An example of a conventional ethanol production process may be found in U.S. Pat. No. 4,885,241, to Millichip entitled "Ethanol production by *zymomonas* cultured in yeast-conditioned media," issued Dec. 5, 1989, the contents of which are hereby incorporated entirely herein by reference.

An example of a conventional biodiesel generating process may be found in U.S. Pat. No. 5,713,965 to Foglia, et al., entitled "Production of biodiesel, lubricants and fuel and lubricant additives," issued Feb. 3, 1998, the contents of which are hereby incorporated entirely herein by reference.

SUMMARY

In one aspect, a first cellulosic ethanol production process may include providing a raw cellulose stream by mixing a waste cellulose stream and an algae cellulose stream and hydrolyzing the raw cellulose stream to form a hydrolyzed cellulose stream by reacting the raw cellulose stream with one or more fungi from the phylum Neocallimastigomycota. The first cellulosic ethanol production process may also include liquefying the hydrolyzed cellulose stream to form a sugars stream, separating the sugars stream to form a xylitol stream and a separated sugars stream, and fermenting the separated sugars stream to form a raw ethanol stream by reacting the separated sugars stream with a yeast feed in at least one fermenter. The first cellulosic ethanol production process also may include separating the raw ethanol stream to form a fuel ethanol stream, generating an algae stream by reacting the xylitol stream with algae in at least one algae bioreactor, and reacting the algae stream in at least one biodiesel reactor to produce the algae cellulose stream and a biodiesel stream.

Implementations of a first process of cellulosic ethanol production may include one, all, or some of the following.

Reacting the raw cellulose stream with one or more fungi may include forming a hydrolysis carbon dioxide ($CO_2$) stream and an ethanol stream.

Liquefying the hydrolyzed cellulose stream may include heating the hydrolyzed cellulose stream and mixing the hydrolyzed cellulose stream with one or more enzymes.

Liquefying the hydrolyzed cellulose stream may include heating the hydrolyzed cellulose stream and mixing the hydrolyzed cellulose stream with one or more bacteria.

Fermenting the separated sugars stream by reacting the separated sugars stream with a yeast feed may produce a fermentation $CO_2$ stream.

Generating the algae stream may include reacting the hydrolysis $CO_2$ stream, the fermentation $CO_2$ stream, and an atmospheric $CO_2$ stream with the xylitol stream in the at least one algae bioreactor.

The one or more fungi from the phylum Neocallimastigomycota may be selected form the group consisting of the genera *Neocallimastix, Piromyces*, and *Orpinomyces*.

The one or more fungi from the phylum Neocallimastigomycota may be selected from the group consisting of *Neocallimastix patriciarum, Neocallimastix patriciarum* strain 27, *Neocallimastix frontalis*, and *Piromyces* sp. strain E2.

Separating the raw ethanol stream may include using at least one molecular sieve.

Separating the sugars in the sugars stream may further include chromatographically separating xylitol from the sugars stream to produce the xylitol stream and the separated sugars stream.

In another aspect, a second cellulosic ethanol production process may include providing a raw cellulose stream by mixing a waste cellulose stream and an algae cellulose stream and hydrolyzing the raw cellulose stream to form a hydrolyzed cellulose stream, a hydrolysis $CO_2$ stream, and an ethanol stream by reacting the raw cellulose stream with one or more fungi selected from the group consisting of the genera *Neocallimastix, Piromyces*, and *Orpinomyces*. The second cellulosic ethanol production process may also include liquefying the hydrolyzed cellulose stream to produce a sugars stream by heating the hydrolyzed cellulose stream and by reacting the hydrolyzed cellulose stream with one or more enzymes, one or more bacteria, or with one or more enzymes in combination with one or more bacteria. The second cellulosic ethanol production process may also include separating sugars stream producing a xylitol stream and a separated sugars stream, fermenting the separated sugars stream to produce a raw ethanol stream and a fermentation $CO_2$ stream by reacting the separated sugars stream with a yeast feed in at least one fermenter, separating the raw ethanol stream producing a fuel ethanol stream and a waste cellulose stream. The second cellulosic ethanol production process may also include generating an algae stream by reacting the hydrolysis $CO_2$ stream, the fermentation $CO_2$ stream, the atmospheric $CO_2$ stream, and the xylitol stream with algae in at least one algae bioreactor and reacting the algae stream in the at least one biodiesel reactor producing the algae cellulose stream and a biodiesel stream.

Implementations of a second cellulosic ethanol production process may include one, all, or some of the following.

The one or more fungi selected from the group consisting of the genera *Neocallimastix, Piromyces*, and *Orpinmyces* may be selected from the group consisting of *Neocallimastix patriciarum, Neocallimastix patriciarum* strain 27, *Neocallimastix frontalis*, and *Piromyces* sp. strain E2.

The one or more enzymes may be selected from the group of α-amylase, β-glucanase, cellobiase, dehydrogenase, exoglucohydrolase, formate, alcohol dehydrogenase E, cytosol, pyruvate formate lyase, lignase, and excrements of cephalopods or ocean mammals.

Separating the sugars in the sugars stream may include chromatographically separating xylitol in the sugars stream to produce the xylitol stream and the separated sugars stream.

In still another aspect, a cellulosic ethanol production system may include a feed stage having a feed operation that includes a grinding operation and a mixing operation. The grinding operation may be configured to produce a waste cellulose stream and the mixing operation may be configured to receive the waste cellulose stream and an algae cellulose stream and produce a raw cellulose stream. A hydrolysis stage may be coupled to the feed stage and configured to receive the raw cellulose stream and include a hydrolysis operation. The hydrolysis operation may be configured to react the raw cellulose stream with one or more fungi from the phylum Neocallimastigomycota in a fungi feed and produce a hydrolyzed cellulose stream, a hydrolysis $CO_2$ stream, and an ethanol stream. A liquefaction stage may be coupled to the hydrolysis stage and may be configured to receive the hydrolyzed cellulose stream from the hydrolysis stage and include a heated sugar formation operation, a fungi separation operation, and a liquefaction operation. The liquefaction operation may be configured to react the hydrolyzed cellulose stream with one or more enzymes, one or more bacteria, or one or more enzymes in combination with one or more bacteria to produce a sugars stream and a recycled fungi stream.

The cellulosic ethanol production system may also include a sugars separation stage coupled to the liquefaction stage configured to receive the sugars stream and including a sugar separation operation and a mash cooling operation, the sugar separation operation configured to produce a xylitol stream and a separated sugars stream. A fermentation stage may be coupled to the sugars separation stage and may be configured to receive the separated sugars stream and may include a fermentation operation. The fermentation operation may be configured to react the separated sugars stream with a yeast feed in at least one fermenter to produce a raw ethanol stream and a fermentation $CO_2$ stream. A separation stage may be coupled to the fermentation stage and may be configured to receive the raw ethanol stream and may include a separation operation. The separation operation may be configured to separate ethanol from the raw ethanol stream to produce a fuel ethanol stream and a waste cellulose stream.

The cellulosic ethanol production system may also include an algae generation stage configured to receive the hydrolysis $CO_2$ stream, the fermentation CO2 stream, an atmospheric $CO_2$ stream, and the xylitol stream and including an algae generation operation. The algae generation operation may include at least one algae bioreactor and may be configured to react the hydrolysis $CO_2$ stream, the fermentation $CO_2$ stream, the atmospheric $CO_2$ stream, and the xylitol stream with algae in the at least one algae bioreactor to produce an algae stream. A biodiesel production stage may be coupled to the algae generation stage and may be configured to receive the algae stream and include a biodiesel reaction operation and an algae drying operation. The biodiesel reaction operation may be configured to produce a biodiesel stream and an algae waste stream. The algae drying operation may be configured to receive the algae waste stream and produce the algae cellulose stream.

Implementations of the cellulosic ethanol production system may include one, all, or some of the following.

The one or more fungi from the phylum Neocallimastigomycota may be selected form the group consisting of the genera *Neocallimastix, Piromyces,* and *Orpinomyces.*

The one or more fungi from the phylum Neocallimastigomycota may be selected form the group consisting of *Neocallimastix patriciarum, Neocallimastix patriciarum* strain 27, *Neocallimastix frontalis,* and *Piromyces* sp. strain E2.

The one or more enzyme may be selected from the group consisting of α-amylase, β-glucanase, cellobiase, dehydrogenase, exoglucohydrolase, formate, alcohol dehydrogenase E, cytosol, pyruvate formate lyase, lignase, and excrements of cephalopods or ocean mammals.

The sugar separation operation may include a chromatographic separator configured to produce the xylitol stream by separating xylitol in the separated sugars stream from the sugars stream.

The foregoing and other aspects, features, and advantages will be apparent from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

This disclosure, its aspects and implementations, are not limited to the specific components or procedures disclosed herein. Many additional components and procedures known in the art consistent with the intended cellulosic ethanol generation systems and processes and/or assembly procedures for a cellulosic ethanol systems and processes will become apparent for use with particular implementations from this disclosure. Accordingly, for example, although particular implementations are disclosed, such implementations and implementing components may comprise any shape, size, style, type, model, version, measurement, concentration, material, quantity, and/or the like as is known in the art for such cellulosic ethanol generating systems and processes and implementing components, consistent with the intended operation.

Structure

Figure 1:
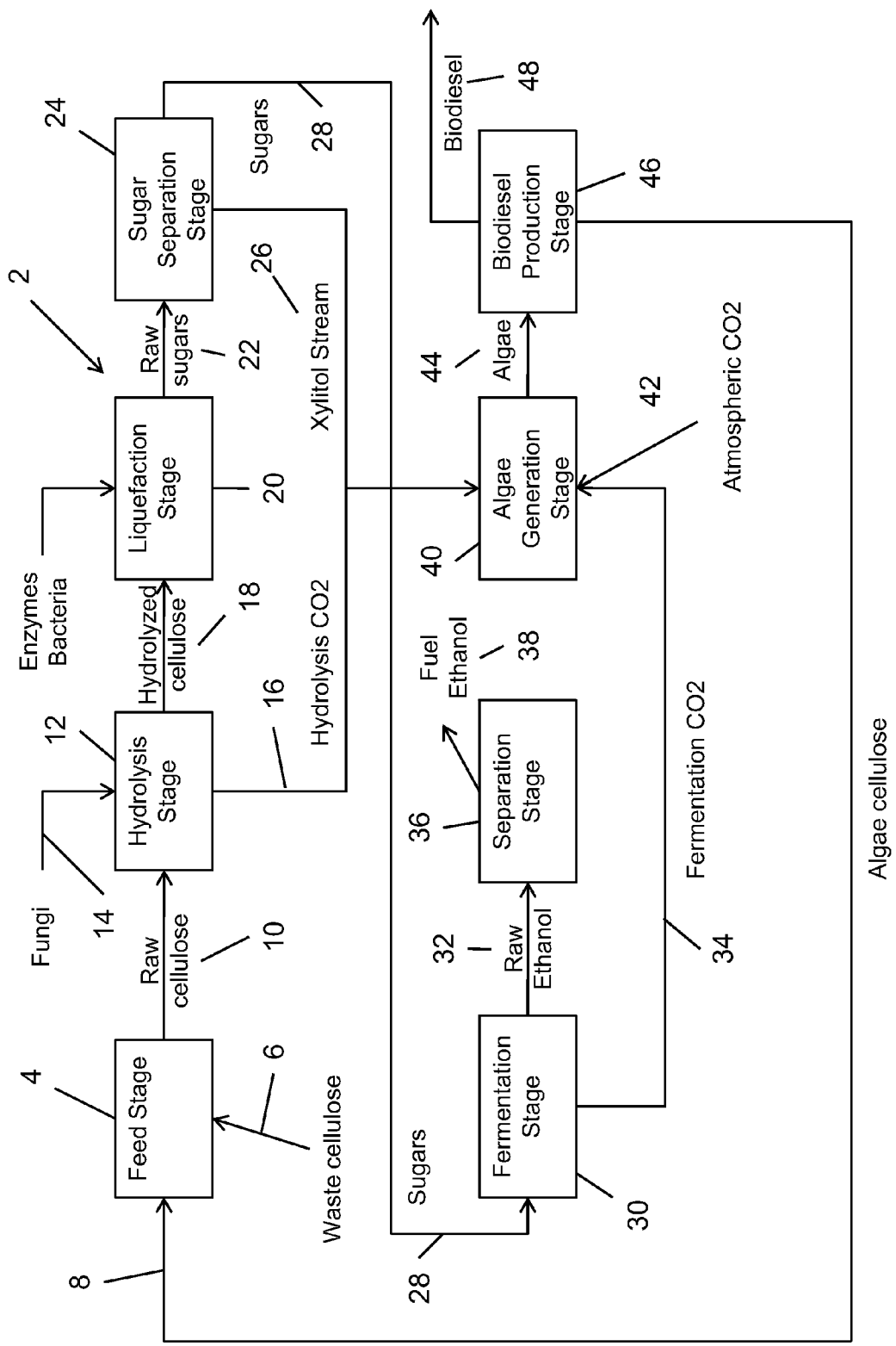
FIG. 1 is a block diagram of a first implementation of a cellulosic ethanol production system.

Referring to FIG. 1, a first implementation of a cellulosic ethanol generating system 2 is illustrated. The system includes a feed stage 4 that includes a mixing operation configured to receive a waste cellulose feed 6 of cellulosic material from biomass ground in a grinding operation. The mixing operation of the feed stage 4 mixes the cellulosic material in the waste cellulose feed 6 with cellulosic material in an algae cellulose feed 8. The cellulosic material in the waste cellulose feed 6 may be derived from any biomass source containing appreciable quantities of cellulose, such as, by non-limiting example, organic landfill waste, paper waste, paper mill process effluent, residential garbage, sawdust, and any other source of cellulosic material, including recycled cellulosic material from the cellulosic ethanol generating system 2 itself. The cellulosic material in the algae cellulose feed 8 may include any cellulosic material derived from algae including, by non-limiting example, living algae, dried algae, algae biodiesel bioreactor effluent, or any other portion of any species of algae used in an algal biodiesel process. The mixing operation of the feed stage 4 combines the cellulosic material in the waste cellulose feed 6 with that in the algae cellulose feed 8 and a certain amount of water to produce a raw cellulose stream 10.

A hydrolysis stage 12 is coupled to the feed stage 4 and is configured to receive the raw cellulose stream 10 and process it in a hydrolysis operation. The hydrolysis operation is configured to react the cellulosic material in the raw cellulose stream 10 with fungi in a fungi feed 14. The hydrolysis operation breaks down the structure of the cellulosic material in the raw cellulose stream 10 by using the fungi to attack lignins, hemicelluloses, celluloses, and cellobioses in the cellulosic material. This breakdown of the cellulosic material may allow later process steps to expose, convert, and release as much glucose and other sugar material from the cellulosic material as possible. As the fungi attack the cellulosic material, they both incorporate it into their own biomass and release free glucoses derived from the broken down lignins, hemicelluloses, celluloses, and cellobioses in the cellulosic material. The fungi may utilize any of a wide variety of enzymes and biological reaction pathways to react the cellulosic material and convert it to a food source. The particular enzymes and biological reaction pathways will depend upon the type of fungi used, the chemical makeup of the cellulosic material in the raw cellulose stream 10, and other relevant process control variables, such as, by non-limiting example, the concentration of enzymes such as alcohol dehydrogenase E, temperature, pressure, light, or any other variable capable of influencing the growth or metabolic process of the fungi or a chemical reaction occurring in the hydrolysis operation. The use of alcohol dehydrogenase E may have the effect of both enhancing and inhibiting the activity of the fungi, depending upon its concentration in the system at a given point in time. Accordingly, varying the concentration of alcohol dehydrogenease E may be used as a method of process control of the hydrolysis operation in particular implementations of cellulose ethanol production systems 2.

The enzymes and biological reaction pathways may allow glucose, ethanol, cellobiose, and other reactive enzymes to be incorporated into the raw cellulose stream 10. During the hydrolysis operation, carbon dioxide ($CO_2$) may be released by the fungi and/or the cellulosic material during the reaction period and may be captured to form a hydrolysis $CO_2$ stream 16. When ethanol is released by the fungi reacting with the cellulosic material, that ethanol may be captured and separated to form a hydrolysis ethanol stream for later use as fuel ethanol.

The fungi in the fungi feed 14 may include any species or combination of species from the phylum Neocallimastigomycota. In particular implementations, species selected from the genera Neocallimastix, Piromyces, and Orpinomyces may be included. For the exemplary purposes of this disclosure, specific species that may be utilized may include Neocallimastix patriciarum, Neocallimastix patriciarum strain 27, Neocallimastix frontalis, and Piromyces sp. strain E2. The fungi in the fungi feed 14 may be naturally occurring species or may have been created by any known type of genetic engineering, such as, by non-limiting example, breeding, recombinant DNA techniques, gene splicing, cloning, hybridization, or any other method of altering or controlling the genetic material of the fungi and/or the expression of the genetic material of the fungi. For the exemplary purposes of this disclosure, the fungi chosen are anaerobic fungi, but in other particular implementations, the fungi may be aerobic or capable of respiration by either aerobic or anaerobic pathways.

The hydrolysis operation may be carried out in any type of container, such as, by non-limiting example, a bioreactor, a vat, a tank, a plurality of bioreactors, or any other container allowing the mixing of the cellulosic material with the fungi in the fungi feed 14. The fungi feed 14 may include a wide variety of other materials intended to assist with the reaction occurring in the hydrolysis stage 12 and/or subsequent stages in the cellulosic ethanol generation process 2. These materials may include, by non-limiting example, fungi nutrients, fungi food sources, enzymes, bacteria, and any other organic or inorganic reagent, chemical or organism that may assist with hydrolysis of the cellulosic material in the raw cellulose stream 10. The fungi in the fungi feed 14 may be at least partially derived from a fungi separation operation or may be totally derived from a separate fungi growing process coupled to the fungi feed 14. The fungi in the fungi feed 14 may be grown at the same site as the cellulosic ethanol generation system 2, or may be cultivated in another location and brought in periodically or continuously as needed. The particular fungi nutrients, fungi food sources, fungi growing processes, and other chemicals used in the hydrolysis operation depend upon the particular fungus or combination of fungal species used.

For the exemplary purposes of this disclosure, the fungus included in the fungi feed 14 may be Piromyces sp. strain E2 and the enzymes and biological reaction pathway utilized to break down the cellulosic material in the raw cellulose stream 10 may be those described in the article by Steenbakkers et al. (hereinafter "Steenbakkers") entitled "β-Glucosidase in cellulosome of the anaerobic fungus Piromyces sp. strain E2 is a family 3 glycoside hydrolase," Biochem. J. 370, 963-970, (2003), the disclosure of which is hereby incorporated entirely herein by reference. In addition, the fungal species, enzymes, and biological reaction pathways detailed by Boxma, et al. (hereinafter "Boxma") in the article entitled "The anaerobic chytridiomycete fungus Piromyces sp. E2 produces ethanol via pyruvate:formate lyase and an alcohol dehydrogenase E," Molecular Microbiology 51(5), 1389-1399 (2004), the disclosure of which is hereby incorporated entirely herein by reference, may be utilized in particular implementations. These references also disclose exemplary techniques and processes for isolating, cultivating, utilizing, growing, and analyzing fungi that may be used in particular implementations of cellulosic ethanol production systems and processes and Steenbakkers and Boxma are specifically incorporated by reference herein for their relevant teachings on these subjects.

After being processed by the fungi in the hydrolysis operation of the hydrolysis stage 12, the cellulosic material in the raw cellulose stream 10 is converted to a hydrolyzed cellulose stream 18. A liquefaction stage 20 is coupled to the hydrolysis stage 12 and is configured to receive the cellulosic material in hydrolyzed cellulose stream 18. The hydrolysis stage 12 may include a fungi separation operation, a heated sugar formation operation, and a liquefaction operation. The fungi separation operation may permit some or all of the fungi in the hydrolyzed cellulose stream 18 leaving the hydrolysis stage 12 to be separated. The separated fungi may be either partially or fully recycled back to the hydrolysis stage, may be partially or fully discarded, or may be partially or fully processed and reintroduced into the hydrolyzed cellulose stream 18 to provide additional cellulosic material for ethanol generation as a recycled fungi stream. The fungi separation operation may occur using any of many techniques known to those of skill in the art, such as, by non-limiting example, centrifugation, settling, or any other method of concentrating and removing fungi from a stream.

The heated sugar formation operation of the liquefaction stage 20 raises the temperature of the hydrolyzed cellulose stream 18 to release sugars from the cellulosic material contained in it. The heated sugar formation operation may be a simple heating step prior to introduction into further process operations or may involve maintaining the hydrolyzed cellulose stream 18 at an elevated temperature for an extended period of time. Enzymes and/or bacterial may be added to the hydrolyzed cellulose stream 18 at this point in particular implementations. For the exemplary purposes of this disclosure, the heated sugar formation operation may be conducted at 80-100 C for an hour and a half. The heated sugar formation operation may take place in any appropriate heating vessel or structure, such as, by non-limiting example, a jet cooker, a heat exchanger, a heated vessel, or any other heat transfer structure capable of raising the temperature of the hydrolyzed cellulose stream 18.

The liquefaction stage 20 may also include a liquefaction operation configured to react the cellulosic material in the hydrolyzed cellulose stream 18 with one or more enzymes and/or one or more bacteria. The liquefaction operation may take place at elevated or ambient temperatures, depending upon the requirements of the particular enzyme and/or bacterium used. The liquefaction operation may serve to further breakdown celluloses and cellobioses into glucoses and other sugars and aid in the overall conversion of the cellulosic material in the hydrolyzed cellulose stream 18 to sugars. Enzymes that may be reacted with the cellulosic material in the hydrolyzed cellulose stream include, by non-limiting example, alpha-amylase, beta-glucanase, cellobiase, dehydrogenase, exoglucohydrolase, formate, alcohol dehydrogenase E, cytosol, pyruvate formate lyase, lignase, and excrements of cephalopods or ocean mammals. The bacteria reacted with the cellulosic material in the hydrolyzed cellulose stream may include any bacterium that is capable of releasing any of the above enzymes or any other enzyme useful in producing sugars from the cellulosic material in the hydrolyzed cellulose stream 18. In other implementations, a fungus may be added to the hydrolyzed cellulose stream to further aid in the conversion of the cellulosic material in the hydrolyzed cellulose stream 18 to sugar. The liquefaction operation, in combination with the fungi separation operation and the heated sugar formation operation, if present, may produce a raw sugars stream 22 and a recycled fungi stream. The raw sugars stream 22 may include a mixture of a number of different sugars, including glucoses and xylitol. The liquefaction operation may take place in any vessel or plurality of vessels capable of handling the cellulosic material in the hydrolyzed cellulose stream 18 and maintaining control of temperature and other relevant process variables.

A sugar separation stage 24 may be coupled to the liquefaction stage and configured to receive the raw sugars stream 22. The sugar separation 24 may include a sugar separation operation and a mash cooling operation. The sugar separation operation may separate fermentable sugars, such as glucoses, from non-fermentable sugars, such as xylitol, thereby helping to increase the productivity of the fermentation operation. The sugar separation operation may take place using a wide variety of techniques known in the art, including, by non-limiting example, chromatography, fractionation, or any other method of separating various sugar molecules by physical property. For the exemplary purposes of this disclosure, the sugar separation operation may occur using a strong base anion resin in a chromatography process, as described in U.S. Pat. No. 6,451,123 to Saska, et al. (hereinafter "Saska") entitled "Process for the Separation of Sugars," issued Sep. 17, 2002, the disclosure of which is hereby incorporated entirely herein by reference. When the separation operation is performed using the process disclosed in Saska, much of the xylitol in the raw sugars stream 22 may be separated, producing a xylitol stream and a sugars stream 28. Because of the separation operation, the sugars stream 28 may contain a substantially greater percentage of fermentable sugars than existed in the raw sugars stream 22.

The mash cooling operation of the sugar separation stage 24 may occur either before, as part of, or after the sugar separation operation in particular implementations. For the exemplary purposes of this disclosure, the mash cooling operation occurs after the sugar separation operation and serves to reduce the temperature of the sugars stream 28 in particular to a level useful for introduction into a fermentation process.

A fermentation stage 30 is coupled to the sugar separation stage 24 and configured to receive the sugars stream 28. The fermentation stage 30 may include a fermentation operation configured to react the sugars stream 28 with a yeast feed to produce a raw ethanol stream 32 and a fermentation CO2 stream 34. The yeasts may consume or ferment the sugars present in the sugars stream 28 and release ethanol, CO2 and other byproducts as a result. The released CO2 may be captured to produce the fermentation CO2 stream 34. The remaining liquid material may pass out of the fermentation stage 30 as the raw ethanol stream 32. The fermentation operation may take place in at least one fermenter under conditions such as, by non-limiting example, a specified period of time, a particular temperature range, in the presence of certain nutrients and any other process variable condition or component useful for the regulation of yeast growth. The yeast included in the yeast feed may be any of a wide variety of fungi and/or bacteria conventionally used to convert glucoses and other sugars to ethanol. For the exemplary purposes of this disclosure, the fungi and/or bacteria may be *Clostridium thermocellum, Piromonas communis* P, or *Zymomanas* sp. The yeasts and/or bacteria used may be either naturally occurring or the product of any form of genetic engineering, such as, by non-limiting example, breeding, recombinant DNA techniques, gene splicing, cloning, hybridization, or any other method of altering or controlling the genetic material of the fungi and/or bacteria and/or the expression of the genetic material of the fungi and or bacteria. Those of ordinary skill in the art will readily be able to select appropriate fermentation conditions, fermenters, and yeasts to produce ethanol using the principles disclosed in this document.

A separation stage 36 may be coupled to the fermentation stage 30 and be configured to receive the raw ethanol stream 32. The separation stage 36 may include a separation operation configured to separate ethanol from the raw ethanol stream 32 and produce a fuel ethanol stream 38 and a waste cellulose stream. The separation operation may include any of a wide variety of separation devices utilizing a number of conventional ethanol separation processes. Some of these may include, by non-limiting example, a molecular sieve, distillation, azeotropic distillation, centrifugation, vacuum distillation, any other method of separating ethanol from water and/or fermentation byproducts. The waste cellulose stream consisting of cellulose-containing materials not converted to ethanol in the process may be reintroduced at the feed stage and mixed to become part of the raw cellulose stream 10 in particular implementations.

An algae generation stage 40 may be included as part of implementations of an cellulosic ethanol production system 2 and may be coupled to the system by being configured to receive the hydrolysis CO2 stream 16, the fermentation CO2 stream 34, an atmospheric CO2 stream 42, and the xylitol stream 26. The algae generation stage 40 may include an algae generation operation that may include at least one algae bioreactor in which the hydrolysis CO2 stream 16, the fermentation CO2 stream 34, an atmospheric CO2 stream 42, and the xylitol stream 26 are reacted with algae. As the algae feed on the CO2 and xylitol contained in the streams, they multiply, and the multiplying algae may be removed from the at least one algae bioreactor as an algae stream 44.

A biodiesel production stage 46 may be coupled to the algae generation stage 40 and be configured to receive the algae stream 44. The biodiesel production stage 46 may include a biodiesel reaction operation and an algae drying operation. The biodiesel reaction operation may be configured to receive the algae stream 44 and process the algae in the stream to obtain biodiesel fuel, producing an biodiesel stream 48 and an algae waste stream. The algae drying operation may be configured to receive the algae waste stream and remove water and other liquids from the stream to produce the algae cellulose stream 8. The algae drying operation may not be included in particular implementations, meaning that the contents of the algae waste stream will pass directly to the algae cellulose stream 8 with little modification. Relevant teachings regarding algae generation and algal biodiesel generation may be found in U.S. Patent Application Publication No. 20070048859 to Sears, entitled "Closed System Bioreactor Apparatus," published Mar. 1, 2007 and in U.S. Patent Application Publication No. 20070048848 to Sears, entitled "Method, Apparatus, and System for Biodiesel Production from Algae," published Mar. 1, 2007 the disclosures of both of which are hereby incorporated entirely herein by reference.

Figure 2:
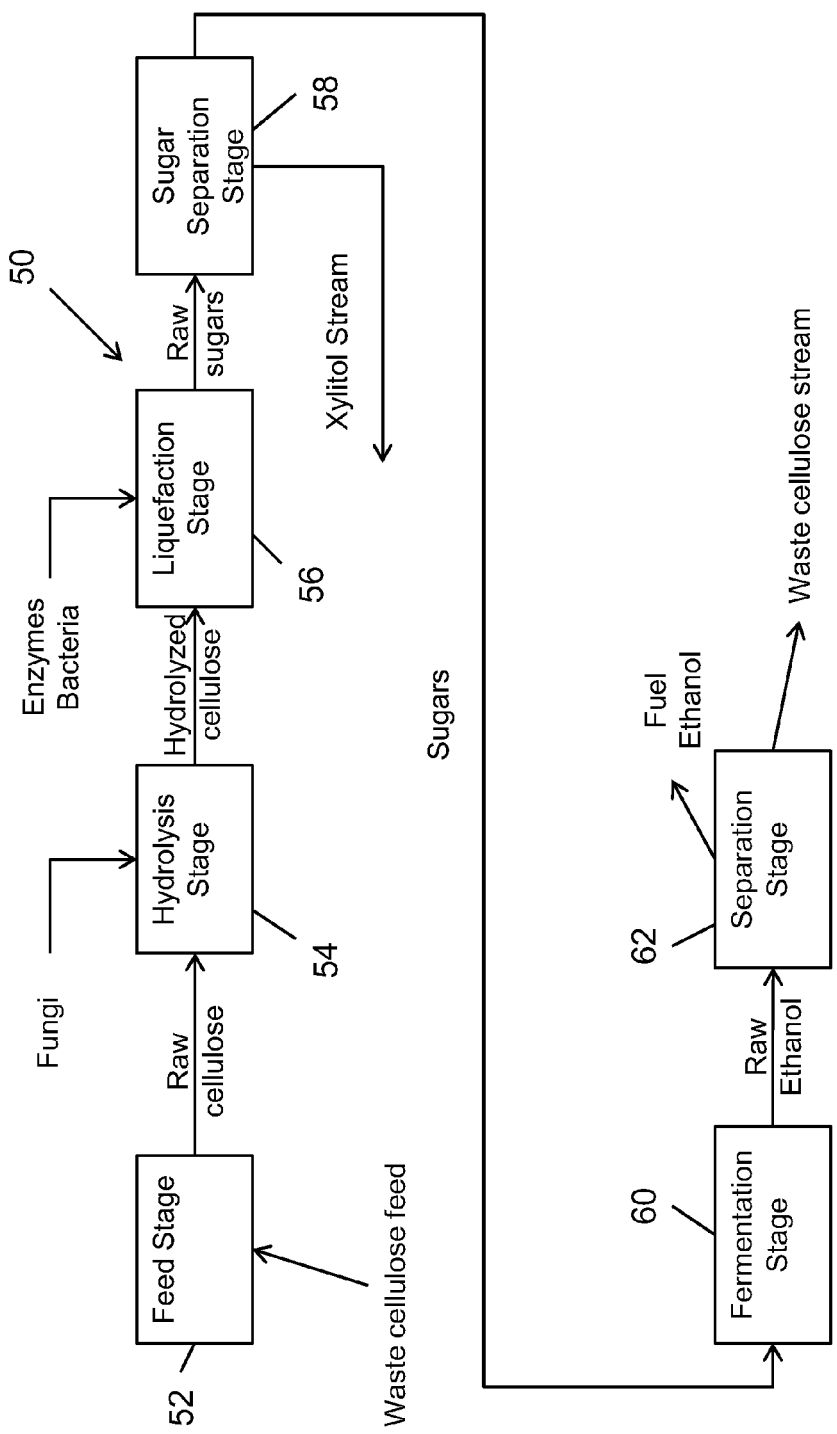
FIG. 2 is a block diagram view of a second implementation of a cellulosic ethanol production system.

Referring to FIG. 2, a second implementation of a cellulosic ethanol production system 50 is illustrated. This implementation may include a feed stage 52, hydrolysis stage 54, liquefaction stage 56, sugar separation stage 58, fermentation stage 60, and separation stage 62 that are configured like and operate similarly to those described in the implementation illustrated in FIG. 1. However, no algae generation or biodiesel production component may be included, as illustrated in FIG. 2. Accordingly, any CO2 generated during the process is not recaptured to grow algae and the xylitol separated at the sugar separation stage 58 is also not used in any algae generation process. Additionally, the only biomass input to this implementation comes in the form of a waste cellulose feed 64 that does not contain any algae biomass generated as part of the cellulosic ethanol production system 50. The foregoing statement does not preclude the use of an implementation of a cellulosic ethanol production system 50 with an algal biodiesel plant, using the waste product of the algal biodiesel plant as a feed stock. However, in such implementations, the algal biodiesel plant would not be fully integrated with the cellulosic ethanol production system 50 by utilizing xylitol and/or CO2 generated as a feed stock for the growth of algae.

Use

Implementations of cellulosic ethanol production systems 2, 50 may utilize implementations of cellulosic ethanol production processes. These processes may include various process steps corresponding with various stages and operations within the cellulosic ethanol production systems 2, 50. Accordingly, implementations of cellulosic ethanol production systems 2, 50 may perform operations such as providing, hydrolyzing, liquefying, separating, fermenting, generating, and reacting, as well as many other functions inherent in the operation of implementations of cellulosic ethanol production systems 2, 50. These cellulosic ethanol production processes may utilize the same fungi, enzymes, and bacteria previously disclosed while performing the various process steps.

For the exemplary purposes of this disclosure, a particular implementation of a cellulosic ethanol production process 2 includes providing a raw cellulose stream 10 by mixing a waste cellulose feed 4 and an algae cellulose feed 8 and hydrolyzing the raw cellulose stream 10 to form a hydrolyzed cellulose stream 18, a hydrolysis CO2 stream 16, and a hydrolysis ethanol stream by reacting the raw cellulose stream 10 with one or more fungi selected from the group consisting of the genus *Neocallimastix, Piromyces*, and *Orpinomyces* in a fungi feed 14. The implementation includes liquefying the hydrolyzed cellulose stream 18 to produce a raw sugars stream 22 by heating the hydrolyzed cellulose stream 18 and by reacting the hydrolyzed cellulose stream 18 with one or more enzymes, one or more bacteria, or with one or more enzymes in combination with one or more bacteria. The implementation also includes separating the sugars in the raw sugars stream 22 to produce a xylitol stream 26 and a sugars stream 28, fermenting the sugars stream 28 to produce a raw ethanol stream 32 and a fermentation CO2 stream 34 by reacting the sugars stream 28 with a yeast feed in at least one fermenter, separating the raw ethanol stream 32 to produce a fuel ethanol stream 38 and a waste cellulose stream. The implementation may also include generating an algae stream 44 by reacting the hydrolysis CO2 stream 16, the fermentation CO2 stream 34, an atmospheric CO2 stream 42, and the xylitol stream 26 with algae in at least one algae bioreactor and reacting the algae stream 44 in the at least one biodiesel reactor producing an algae cellulose feed 8 and a biodiesel stream 48.

For implementations of cellulosic ethanol production systems 50, the process steps of generating the algae stream and reacting the algae stream to produce a biodiesel stream and an algae cellulose feed would be absent.

It will be understood that implementations are not limited to the specific components disclosed herein, as virtually any components consistent with the intended operation of a method and/or system implementation for cellulosic ethanol production systems and processes may be utilized. Accordingly, for example, although particular sugar separators, reactors, fungi, and enzymes may be disclosed, such components may comprise any shape, size, style, type, model, version, class, grade, measurement, concentration, material, weight, quantity, and/or the like consistent with the intended operation of a method and/or system implementation for cellulosic ethanol production systems and processes may be used.

In places where the description above refers to particular implementations of cellulosic ethanol production systems and processes, it should be readily apparent that a number of modifications may be made without departing from the spirit thereof and that these implementations may be applied to other cellulosic ethanol production systems and processes.

Testing

An experiment was performed using *Piromyces* sp. E2 to determine an exemplary amount of fungi organelles required per ton of biomass as a function of the potential percentage of available sugar in the biomass varied. This experiment was used to determine an equation for the number of organelles per ton of biomass. The experimental results are listed below in Table 1. Similar results were seen for a combination of *Neocallimastix* sp. L2 and *E. coli*.

TABLE 1

Actual Incubation of *Piromyces* sp. E2 (in 0.005 gallons) & Growth (Lbs of wt)

| Organilles | Sugar Avail | Hydrogen | Ethanol | Biomass Remain | Time (hrs) |
|---|---|---|---|---|---|
| 1.77 | 30.00% | 0.00002 | 0.00005 wgt/vol | 2.06 | 16 |
| 1.97 | 35.00% | 0.00002 | 0.00006 wgt/vol | 2.30 | 16 |
| 2.81 | 40.00% | 0.00003 | 0.00008 wgt/vol | 3.28 | 16 |
| 3.82 | 45.00% | 0.00003 | 0.00011 wgt/vol | 4.45 | 16 |
| 5.63 | 50.00% | 0.00005 | 0.00016 wgt/vol | 6.56 | 16 |
| 7.64 | 55.00% | 0.00007 | 0.00022 wgt/vol | 8.91 | 16 |
| 9.65 | 60.00% | 0.00009 | 0.00027 wgt/vol | 11.25 | 16 |
| 11.66 | 65.00% | 0.00011 | 0.00033 wgt/vol | 13.59 | 16 |

The resulting equation was $y=0.000x+29.07$ where y is the number of organelles per ton of biomass and x is the percentage of available sugar in the biomass.

The invention claimed is:

1. An integrated process to produce fuel ethanol and biodiesel from cellulose comprising:

providing a raw cellulose stream to one or more containers selected from the group consisting of a vat, a bioreactor, and a tank by mixing a waste cellulose stream and an algae cellulose stream;

hydrolyzing the raw cellulose stream to form a hydrolyzed cellulose stream by reacting the raw cellulose stream with one or more fungi from the phylum Neocallimastigomycota;

liquefying the hydrolyzed cellulose stream to form a sugars stream;

separating the sugars stream to form a xylitol stream and a separated sugars stream;

fermenting the separated sugars stream to form a raw ethanol stream by reacting the separated sugars stream with a yeast feed in at least one fermenter;

separating the raw ethanol stream to form a fuel ethanol stream;

producing an algae stream by reacting the xylitol stream with algae in at least one algae bioreactor; and reacting the algae stream in at least one biodiesel reactor to produce the algae cellulose stream and a biodiesel stream; and recovering the fuel ethanol and the biodiesel from their respective streams.

2. The process of claim 1, wherein reacting the raw cellulose stream with one or more fungi further comprises forming a hydrolysis carbon dioxide $CO_2$ stream and an ethanol stream.

3. The process of claim 1, wherein liquefying the hydrolyzed cellulose stream further comprises heating the hydrolyzed cellulose stream and mixing the hydrolyzed cellulose stream with one or more enzymes.

4. The process of claim 1, wherein liquefying the hydrolyzed cellulose stream further comprises heating the hydrolyzed cellulose stream and mixing the hydrolyzed cellulose stream with one or more bacteria.

5. The process of claim 2, wherein fermenting the separated sugars stream by reacting the separated sugars stream with a yeast feed produces a fermentation $CO_2$ stream.

6. The process of claim 5, wherein producing the algae stream further comprises reacting the hydrolysis $CO_2$ stream, the fermentation $CO_2$ stream, and an atmospheric $CO_2$ stream with the xylitol stream in the at least one algae bioreactor.

7. The process of claim 1, wherein separating the raw ethanol stream includes using at least one molecular sieve.

8. The process of claim 1, wherein separating the sugars stream further comprises chromatographically separating xylitol from the sugars stream to produce the xylitol stream and the separated sugars stream.

* * * * *